United States Patent
Khosravani et al.

(10) Patent No.: US 9,884,987 B2
(45) Date of Patent: Feb. 6, 2018

(54) COMPOSITIONS AND METHODS EMPLOYING MULTI-WALLED CARBON NANOTUBE-BASED NANOHYBRIDS AND APPLICATIONS THEREOF IN OIL RECOVERY

(71) Applicants: Sara Khosravani, Tehran (IR); Mahshid Ershadi, Tehran (IR); Mahshad Alaei, Tehran (IR); Amir Hossein Bornaee, Tehran (IR); Alimorad Rashidi, Tehran (IR); Ali Ramazani, Zanjan (IR); Mehrdad Manteghian, Tehran (IR)

(72) Inventors: Sara Khosravani, Tehran (IR); Mahshid Ershadi, Tehran (IR); Mahshad Alaei, Tehran (IR); Amir Hossein Bornaee, Tehran (IR); Alimorad Rashidi, Tehran (IR); Ali Ramazani, Zanjan (IR); Mehrdad Manteghian, Tehran (IR)

( * ) Notice: Subject to any disclaimer, the term of this patent is extended or adjusted under 35 U.S.C. 154(b) by 239 days.

(21) Appl. No.: 14/622,908

(22) Filed: Feb. 15, 2015

(65) Prior Publication Data
US 2015/0225639 A1 Aug. 13, 2015

Related U.S. Application Data

(60) Provisional application No. 61/939,756, filed on Feb. 14, 2014.

(51) Int. Cl.
  C09K 8/58 (2006.01)
  G01B 21/22 (2006.01)
  G01N 33/24 (2006.01)

(52) U.S. Cl.
  CPC .............. *C09K 8/58* (2013.01); *G01N 33/24* (2013.01); *C09K 2208/10* (2013.01)

(58) Field of Classification Search
  None
  See application file for complete search history.

(56) References Cited

U.S. PATENT DOCUMENTS

2013/0259808 A1* 10/2013 Chen .................. H01B 1/00
                                                      424/9.3

* cited by examiner

*Primary Examiner* — Jeffrey Washville
(74) *Attorney, Agent, or Firm* — NovoTechIP International PLLC (57) ABSTRACT

Nanohybrid preparation methods and compositions, and their usage as oil/water emulsion stabilizers for Chemical Enhanced Oil Recovery (C-EOR). These methods have two main steps: (a) MWCNTs modification; and (b) encapsulation and insertion techniques to insert inorganic nanoparticles into the modified MWCNTs structure. The so-prepared nanohybrids used for the preparation of nanofluids were found to decrease the oil surface tension and reservoir wettability modification from oil-wet to water-wet, which is useful for Chemical Enhanced Oil Recovery (C-EOR).

15 Claims, 10 Drawing Sheets

COMPOSITIONS AND METHODS EMPLOYING MULTI-WALLED CARBON NANOTUBE-BASED NANOHYBRIDS AND APPLICATIONS THEREOF IN OIL RECOVERY

CROSS REFERENCE TO RELATED APPLICATION

The present invention claims priority from U.S. Provisional Patent Application Ser. No. 61/939,756, filed Feb. 14, 2014, entitled "Synthesis of MWCNT-SiO2/Al2O3 Nanohybrids as Pickering Emulsion Forming Agent for Enhanced Oil Recovery Applications," the subject matter of which is incorporated by reference herein in its entirety.

SPONSORSHIP STATEMENT

This application has been sponsored by the Iranian Nanotechnology Initiative Council, which does not have any rights in this application.

TECHNICAL FIELD

The present invention generally relates to enhanced oil recovery, and more particularly, the invention is directed to multi-walled carbon nanotube (MWCNT)-based Nanohybrids, synthesizing the same, and the use thereof in enhanced oil recovery (hereinafter "EOR") and other uses of nanofluids.

BACKGROUND OF THE INVENTION

As is well known in the art, primary oil recovery methods recover only about 15% of the oil in the reservoir, and classical secondary recovery methods, such as water flooding, extracts only about 30% of the oil. This means that more than 60% of the oil is entrapped in the holes and pores of the oil reservoir even after the employment of conventional EOR processes. This is due to the formation of a system called oil-wet in the reservoir, in which the remaining oil in the reservoir sticks to the reservoir rock as a thin layer and wets the rock. Therefore, as is well known to a person skilled in the art, to further increase oil extraction efficiency via separating the remaining oil from the rock surface, it is necessary to change the wettability of the reservoir from an oil-wet system to a hydrophilic or water-wet system.

Accordingly, the wettability of the reservoir can be modified using complementary methods, such as chemical enhanced oil recovery (hereinafter "C-EOR"). As is known in the art, in C-EOR methods, oil extraction efficiency is increased by injecting chemical compounds into the reservoir. The properties of these chemical compounds can be modified, such as by using techniques in the field of nanotechnology to create novel chemical compounds, which, in turn, can significantly improve the efficiency of C-EOR. In this method, the efficiency of the well can be increased by using nanofluids, nanoparticles, nano-surfactants, and nano-composite hydrogels via the formation of a Pickering emulsion (an emulsion stabilized with solid nanoparticles) from the injected nanoparticles and the oil existing in the reservoir, facilitating the movement ability of the oil inside the reservoir, and decreasing the interfacial tension between the oil and water.

Different mechanisms are known in the art for the use of nanotechnology in EOR purposes, such as the use of polymeric nanocomposites, production and application of emulsions and nano-emulsions in enhanced oil recovery, the use of nano-surfactants, and injection of metallic nanomaterials into heavy oil reservoirs in order to increase thermal conductivity of the oil.

However, it should be understood that although many methods have been disclosed in the art on the application of nanoparticles in enhanced oil recovery, the efforts have so far led to only small improvements in the extraction of oil. The reason is that there are some parameters affecting the performance of the injected nanomaterials into the oil reservoirs which should be taken into consideration. As is well known in the art, nanoparticles do not disperse well in oil/water emulsions, and to overcome this issue, a method must be used to prolong the homogenous stability of nanoparticles in the oil/water emulsions.

The general use of carbon nanotube-based nanohybrids to increase the dispersion quality of the nanoparticles in the oil/water emulsions, as well as their stability, is shown in the prior art. However, CNT-based nanohybrids having both hydrophilic and hydrophobic sides, so that they can decrease the surface tension between the oil and the rocks, lead to a more desirable wettability in the reservoir, and consequently increase the oil recovery efficiency, are not shown in the art. However, it should be understood that the methods used to synthesize the aforementioned nanohybrids play an important role in the achievement of the aforementioned properties for the nanohybrids.

Functionalizing the carbon nanotubes, using a mixture of nitric acid and sulfuric acid to add hydrophilic properties to the nanohybrids, is also known in the art. However, this functionalizing method is difficult and time-consuming, and it is not a cost-effective method when used on larger scales in the oil and gas industry. Another drawback of the aforementioned method is that the prepared emulsion using as-produced nanohybrids is stable for only 10 days, and moreover, the water and oil contact angle is only changed about 10 to 20 degrees, which, as is known in the art, is not enough for a significant improvement in EOR efficiency. In addition, in some methods disclosed in the prior art, nanohybrid synthesis is carried out in a reactor, which is a costly method due to the need for complicated devices and instruments.

It should be understood, that the stability of the resultant emulsion is directly affected by the method used to embed nanoparticles into the CNT structure. For instance, coating CNTs on commercial silica nanoparticles is also shown in the prior art, resulting in an emulsion which is stable for a relatively short time.

It is, therefore, an object of the present invention to overcome the limitations, drawbacks and difficulties still existing in synthesizing, and employing nanohybrids in enhanced oil recovery applications.

It is also an object of the present invention to reduce the time and cost of the synthesis method of the aforesaid nanohybrids via using fewer additives and using inexpensive equipment.

It is a further object of the present invention to provide strong structures of CNTs-based nanohybrids, well dispersed in oil/water emulsions, which remain stable for a long time.

Also, an additional object of the present invention is to improve the EOR process using the aforementioned nanohybrids.

These and many other objects are met in various embodiments of the present invention, offering significant advantages over the known prior art and consequent benefits in the extraction techniques.

SUMMARY OF THE INVENTION

The present invention employs the ability of inorganic silica and alumina nanoparticles in conjunction with organic multi-walled carbon nanotubes (MWCNTs) to improve the wettability of reservoir rocks and to reduce interfacial tensions (IFT) between crude oil and salty water for chemical enhanced oil recovery (C-EOR) purposes. The prepared nanohybrids herein are a type of new compounds containing hydrophilic carbon nanotubes bonding with a hydrophobic inorganic part, such as silica or alumina, having specific properties. It should be considered that due to the unique properties of carbon nanotubes and silica/alumina nanoparticles, the aforementioned hybrids can be used as stabilizers of water-in-oil emulsions. The difference in the structure and hydrophilicity and hydrophobicity of these two-part materials result in the formation of compounds appropriate for the creation of Pickering emulsions.

The MWCNTs/Silica or Alumina nanohybrids pursuant to the teachings of the present invention are preferably prepared through a number of methods having two main steps: first, opening and modifying MWCNTs; and second, simultaneous formation and encapsulation of inorganic nanoparticles into the modified MWCNTs structure.

The methods described in the present invention for synthesizing MWCNTs/nanoparticles hybrids are simple and cost-effective, and the prepared products demonstrate both high efficiency and quality, especially for larger scale applications.

Accordingly, the nanohybrids of the instant invention, having hydrophilic-hydrophobic properties, as inter-phase modifier agents, are strongly appropriate for use in C-EOR processes to enhance oil recovery. In the so-prepared nanohybrid structures of the instant invention, the nanoparticles have been placed inside, on the surface, and on the end of carbon nanotubes, forming a stronger hybrid structure. The fluids containing said synthesized nanohybrids are stable for a couple of months without the formation of sediments, and also without using surfactants or co-surfactants, such as alcohols or polymers. Furthermore, the aforementioned functionalization of MWCNTs results in hydrophilicity of nanohybrids, and makes them capable of forming stable oil-in-water emulsions.

In one embodiment of the present invention, interfacial tension (IFT) test results represent a significant decrease of IFT value between oil and water using the prepared silica/alumina nanohybrids. The IFT between oil samples, i.e., ISOMAX kerosene, and distilled water has been reduced about 50% without using any surfactant or co-surfactant, such as alcohols or polymers. The significant reductions in IFT caused by the aforesaid nanoparticles have not been observed in the prior art. The prepared nanohybrids can be proposed as stabilizers of Pickering emulsions in two-phase systems, such as oil/distilled water, oil/salty water, and oil/formation water.

In a further embodiment of the present invention, the produced nanohybrids change the wettability of carbonated and sand rocks from oil-wet to water-wet enhancing the oil recovery from such reservoirs. In particular, the contact angle has been increased about 50-60 degrees in carbonated rocks using the aforesaid nanohybrids.

Since the formation water in the oil reservoirs contains several cations, the positive effect of salts with high concentration on nanohybrids can increase the possibility of their use in EOR processes at real conditions. Since one of the EOR methods is the use of surfactants for decreasing the surface tension and for changing the wettability, it is clear that the use of surfactants in addition to the nanohybrid significantly decreases or even eliminates the surface tension. Reduction in surface tension between oil and water in reservoirs and changing the wettability of reservoir rock from oil-wet to water-wet result in the movement of the trapped oil, and increases the oil extraction efficiency from reservoirs up to 90%.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying DRAWINGS, where like reference numerals designate like structural and other elements, in which:

FIG. 2 further shows the same characterization analysis results as with parts a and b hereinabove, but for MWCNT-$SiO_2$ nanohybrid samples prepared by a sol-gel method pursuant to the teachings of the present invention, as described in more detail in connection with EXAMPLE 3, which include: an XRD pattern, shown in part c, and a scanning electron microscope (SEM) image, shown in part d, respectively;

FIG. 4 further shows the same characterization analysis results as with parts a and b hereinabove, but for MWCNT-Alumina nanohybrid samples prepared by a hydrothermal method by sodium pursuant to the teachings of the present invention, as described in more detail in connection with EXAMPLE 4, which include: an XRD pattern, as shown in part c, and a scanning electron microscope (SEM) image, as shown in part d, respectively;

DETAILED DESCRIPTION OF THE INVENTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

It should be understood to a person skilled in the art that the present invention is directed to a number of methods for the simple, economic and efficient synthesis of multi-walled carbon nanotube-based (or MWCNT-based) nanohybrids with binary hydrophilic-hydrophobic properties. The prepared nanohybrids, pursuant to the methods described in the present invention, significantly alter and improve the wettability of rock reservoirs, i.e., carbonate and sandstone, besides the aforenoted reduction of interfacial tension (IFT) between oil and water without using any surfactant or co-surfactant, proposing a new class of applicable materials for chemically-enhanced oil recovery (C-EOR) applications.

The aforementioned nanohybrids are preferably made of a multi-walled carbon nanotube base, i.e., the hydrophobic part, and a plurality of dispersed inorganic nanoparticles inserted into the structure of said nanotubes, i.e., the hydrophilic part. In some embodiments of the present invention, it should be understood that the hydrophilic nanosized inorganic component is preferably a silica or alumina.

It should also be understood that methods used to synthesize the nanohybrid affect its structure and properties. In the present invention, a number of effective and simple methods are disclosed. MWCNT-silica or -alumina nanohybrids prepared by these methods have been proven most effective since they are synthesized simultaneously during the preparation of silica or alumina nanoparticles.

The nanohybrid preparation methods pursuant to the teachings of the present invention have two main steps: first, opening and modifying the MWCNTs to modify their structure and properties; and secondly, simultaneous production and insertion of nanoparticles into the open-capped MWCNTs structure. It should be understood that the second step can be carried out through different chemical synthesis methods for silica/alumina nanoparticles, such as the sol-gel and hydrothermal methods used in the present invention described further hereinbelow. The aforementioned synthesis-insertion methods can be assisted and enhanced by sonication or chemical compounds. The aforementioned steps are discussed in more detail hereinbelow.

1. Modification of MWCNTs

It should be understood that depending on hydrophilicity, the nanofluid can form an oil-in-water (O/W) or a water-in-oil (W/O) emulsion at the reservoir conditions. Therefore, MWCNTs should be modified to enhance their hydrophilicity for producing O/W emulsions. In the present invention, nitric acid is used to enhance the MWCNTs hydrophilicity for producing these O/W emulsions. Oxidization by nitric acid, as is known from prior art, is a convenient way for grafting functional groups (—COOH) on wall defects, and particularly at the ends of MWCNT, a process that greatly changes the hydrophilicity of MWCNTs. By controlling the extent of MWCNT functionalization, one can manipulate the resulting emulsion properties. In the present invention, the closed ends of multi-walled carbon nanotubes are opened and functionalized due to the reflux with nitric acid instead of oxidation.

2. Nanoparticles Synthesis and Encapsulation

As mentioned hereinabove, the encapsulation and insertion of the silica/alumina nanoparticles into the MWCNTs structure is carried out substantially simultaneously during the synthesis of the nanoparticles. This step of nanohybrid preparation is preferably done via different methods, further described hereinbelow.

For example, in one embodiment of the present invention, the second step in the aforesaid nanohybrid preparation procedure, preferably in preparing MWCNTs/Silica nanohybrids, is carried out by the well-known sol-gel method. As is understood in the art, the aforementioned sol-gel method can preferably be assisted by ultrasound irradiation to improve the properties of the prepared nanohybrids.

In another embodiment of the present invention, the second step in the nanohybrid preparation procedure, preferably in preparing MWCNTs/Alumina nanohybrids, is carried out by the well-known hydrothermal method. In some embodiments of the present invention, the aforementioned hydrothermal method can be aided and improved using chemical compounds, preferably ammonia or sodium hydroxide or other similar chemical compounds.

It should be considered that the carbon nanotube-to-silica or nanotube-to-alumina weight ratio is an important factor influencing the performance of the synthesized nanohybrid. In a presently preferred embodiment of the present invention, for example, the carbon nanotube-to-inorganic nanoparticles weight ratio is preferably about 30% or less, e.g., 25-30%, 20-25%, 15-20% and 10-15%.

Nanohybrid Emulsification

In a preferred embodiment of the present invention, the emulsification properties of the aforementioned prepared MWCNTs-based nanohybrids are investigated. Two effective factors are studied herein in the nanohybrids emulsification, including: the effect of present cations in the water, and the effect of the mixing strategy or technique employed. The aforesaid study is very important, because the formation water or ambient water presented in oil reservoirs contains high concentrations of several cations. Moreover, it is important that the prepared nanohybrids in the present invention would be active emulsifiers without any external mixing within the reservoirs.

Nanohybrids Application in C-EOR Processes

In a preferred embodiment of the present invention, a nanofluid containing the aforementioned prepared nanohybrids is employed to decrease the oil-water interfacial tension, and to increase the contact angle between rock samples and oil in order to increase the oil recovery.

It should be understood that oil cannot move in porous media of rock, and is trapped due to the pressure difference in the porous environment of the rock, which is caused by the difference in interfacial tension between water and oil. That is why the surface tension should be reduced, so that the pressure difference decreases and oil can leave the environment. The pressure is called capillary pressure and is calculated by the following equation:

$$P_C = \frac{2\sigma_{o-w} \cos\theta}{r}$$

In the above equation, $\sigma$ represents the interfacial tension between water and oil (IFT), r is the radius of pores, and $\theta$ is the contact angle. The value of r is constant for a reservoir formation. Therefore, the capillary pressure is altered due to a change in one or both of the other two parameters, namely, the interfacial tension and the contact angle. The contact angle ($\theta$) is the angle between the tangent line on the surface of the drop in the contact point with the solid surface, which is calculated from the inside of the denser phase (water), and varies from 0° to 180°. If the contact angle between oil and rock is calculated in the oil media, as the contact angle becomes greater than 90°, the sample is more hydrophilic, and vice versa. Also, such wettability alterations can result in a difference in pressure between two sides of reservoir rock porous media that is created because of the difference in interfacial tension between water and oil within the rock.

According to the abovementioned facts, efforts are made to decrease the interfacial tension and increase the contact angle in oil phase to change the wettability of the reservoir from oil-wet to water-wet.

The obtained results described in the EXAMPLES set forth hereinbelow show that nanohybrids pursuant to the instant invention cause a significant decrease in oil-water interfacial tension, and also an increase in the contact angle, meaning that the rock wettability alters from oil-wet to water-wet, without applying any surfactants. Therefore, the residual oil trapped on the rock surface after initial recovery can now, utilizing the principles and techniques of the present invention, exit from the porous media, and be removed efficiently.

Exemplary techniques for the production of MWCNTs-Silica or MWCNTs-Alumina nanohybrids and their use thereof in C-EOR applications, pursuant to the teachings of the present invention, are set forth hereinbelow. It should be understood that these examples are illustrative only, and similar techniques for the production and application of the preferred nanohybrids of the instant invention are thus possible with different parameters, as is well understood to those of skill in the art. Furthermore, the examples set forth herein are exemplary only and should not be deemed as limiting the scope of the present invention. The only limitations of the scope of the instant case are set forth in the claims appended hereinbelow.

Example 1: Preparation of Open-Capped MWCNTs

In the present invention, the supplied MWCNTs are preferably prepared by a chemical vapor deposition (CVD) method, which is known in the prior art, and, after thermal treatment for removing the amorphous carbon, the MWCNTs are treated with HCl and $HNO_3$ for removing the metal oxides.

As described hereinabove, it is necessary to open the caps of MWCNTs for the preparation of the $MWCNT-SiO_2$ and $MWCNT-Al_2O_3$ nanohybrids. Therefore, about 2 g of MWCNT was added to a mixture of about 160 ml distilled water and about 140 ml nitric acid, and the admixture was refluxed for about 18 hours. After filtration and neutralization with distilled water, the resultant sample was kept in an oven to dry.

Figure 1:
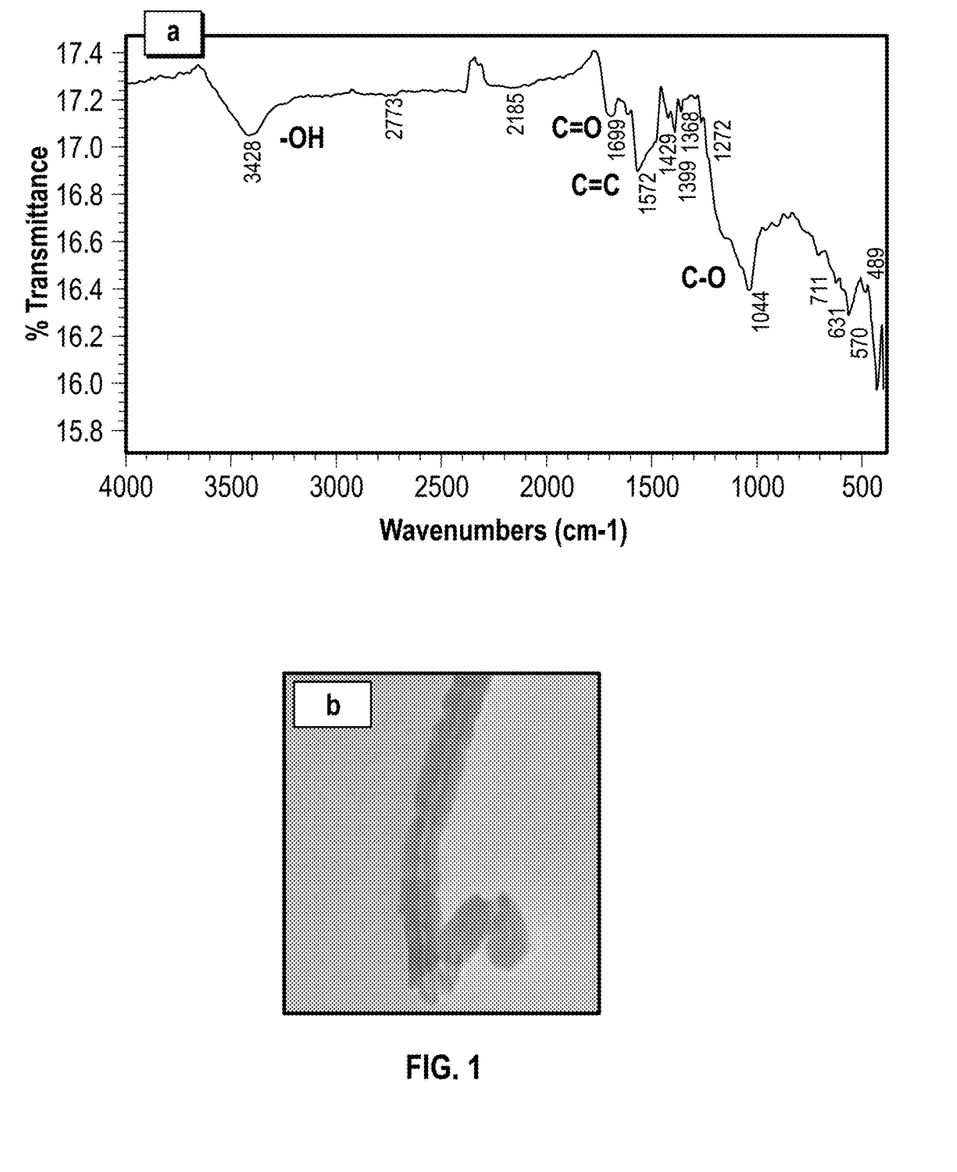
FIG. 1 illustrates characterization analyses results for open-capped MWCNTs prepared pursuant to the teachings of the present invention, which include, respectively, a Fourier-transform infrared (FT-IR) spectra, shown in part a, and a transmission electron microscope (TEM) image of the MWCNTs, shown in part b.

With reference now to FIG. 1 of the DRAWINGS, divided into an upper portion, part a, and a lower portion, part b, the COOH group formation on the MWCNTs structure is proved by the illustrated FT-IR spectra and TEM image of the modified MWCNTs. As shown, the FT-IR studies have been performed in the range of about 400 to 4000/$cm^{-1}$ for identification of the functional groups attached on the surface of the MWCNTs. As shown in part a of FIG. 1, the FT-IR spectra of oxidized MWCNT shows four major peaks, located at 1044, 3428, 1699 and 1572 cm$^{-1}$. The peak at 3428 cm$^{-1}$ can be assigned to the O—H stretch from carboxyl groups (O=C—OH and C—OH). The peak at 1699 cm$^{-1}$ is attributed to the C=O stretching mode of carboxylic acids. Accordingly, the peak at 1572 cm$^{-1}$ refers to the C=C stretching mode, which originates from the backbone of MWCNT. Additionally, the peak at 1044 cm$^{-1}$ is assigned to the C—O stretching vibration. With further reference to part b of FIG. 1, there is shown a transmission electron microscope (TEM) image, depicting opened-capped MWCNTs formed by the aforedescribed refluxing process with nitric acid.

Example 2: Synthesis of the MWCNT-Silica Nanohybrids by a Sol-Gel Method Under Ultrasound Irradiation In this embodiment example, about 7 ml tetraethyl orthosilicate (TEOS) was dissolved in about 35 ml ethanol, and put in ultrasonic bath for about 20 minutes afterwards, after which about 1 ml distilled water was added to the mixture and a suitable amount of the aforementioned open-capped MWCNTs, prepared as described in connection with EXAMPLE 1 hereinabove, was added and stirred for about 10 minutes. Then, about 2 ml ammonia solution (25%) was added into the reaction mixture at a rate of about 0.2 ml min$^{-1}$ as the reaction catalyst. Thereafter, the obtained mixture was sonicated for about 3 hours. Finally, the product was filtered and washed with distilled water and ethanol and dried in the oven at 60° C.

Figure 2:
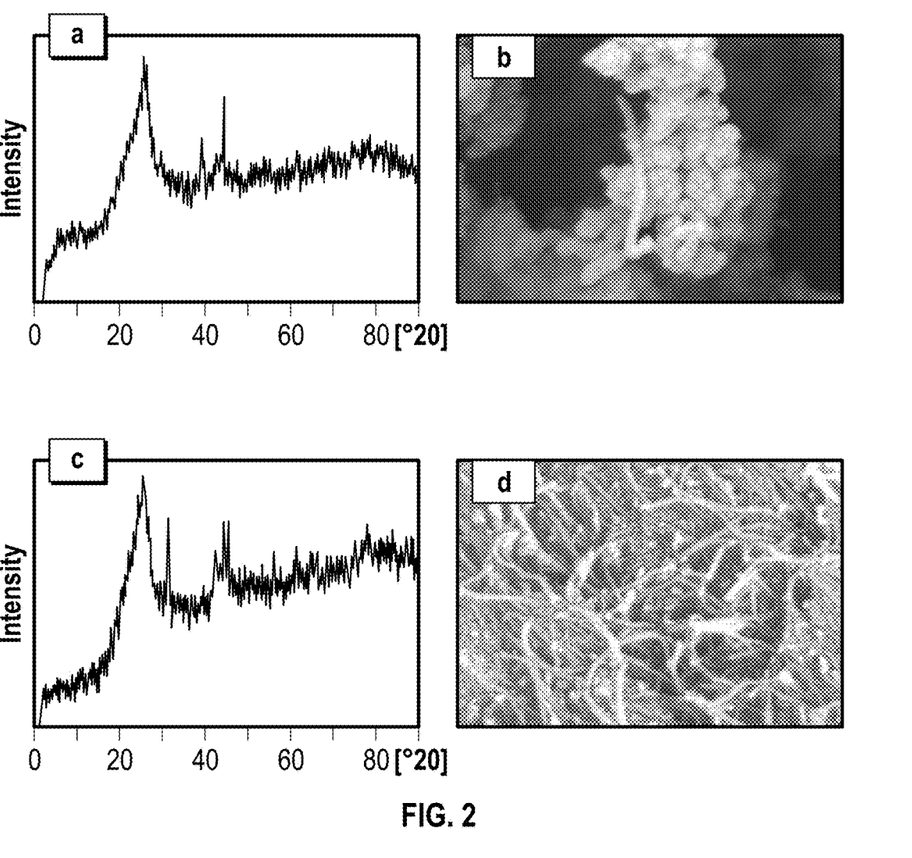
FIG. 2 shows characterization analyzes results for prepared MWCNT-$SiO_2$ nanohybrid samples by a sol-gel method under ultrasound irradiation pursuant to the teachings of the present invention, as described in more detail in connection with EXAMPLE 2, which include: an X-Ray Diffraction (XRD) pattern, shown in part a, and a scanning electron microscope (SEM) image, shown in part b, respectively.

With reference now to FIG. 2 of the DRAWINGS, divided into four images, parts a, b, c and d, respectively, there are shown a pair of X-Ray Diffraction (XRD) patterns and SEM images of the prepared MWCNT-SiO$_2$, as illustrated in parts a and b, and the nanohybrid, as illustrated in parts c and d, respectively. The XRD patterns show the existence of both of SiO$_2$ nanoparticles and MWCNTs in the structure of the prepared MWCNT-SiO$_2$ nanohybrid.

Figure 3:
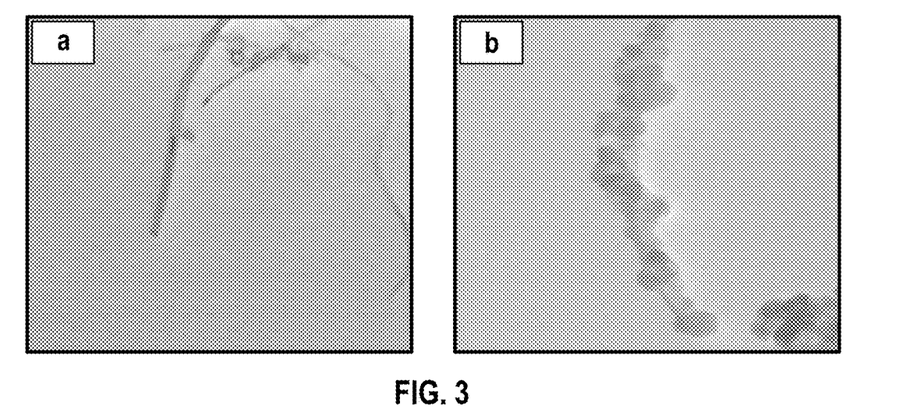
FIG. 3 shows transmission electron microscope (TEM) images of MWCNT-$SiO_2$ nanohybrid samples prepared by the methods described in more detail in connection with EXAMPLE 2, part a, and EXAMPLE 3, part b, respectively.

With reference now to FIG. 3 of the DRAWINGS, there is shown a TEM image of the MWCNT-SiO$_2$ nanohybrid produced by the method described herein, particularly pursuant to the aforesaid Example 2, shown in part a, and pursuant to Example 3 hereinbelow, shown in part b. As can be seen, the silica nanoparticles have been inserted both interiorly and on the surface of the MWCNTs. The formation of this structure is superior to any related inventions disclosed in the prior art, particularly where silica nanoparticles coat only the surface of MWCNTs.

Example 3: Synthesis of the MWCNT-Silica Nanohybrids by a Sol-Gel Method

Here, about 0.7 g of MWCNTs was added to about 3 ml sodium silicate in order to produce MWCNT-SiO$_2$ nanohybrids by the sol-gel method. The open-capped MWCNT was kept in about 50 mL of 2.5% hydrochloric acid at about 80° C. with a stirring rate of about 300 rpm until it was fully distributed. Afterwards, the sodium silicate solution was transformed by dripping into the mixture with the rate of about 10 drops per minute until forming a viscous and cloudy gel. Finally, the obtained product was dried at about 80° C. for 24 hours. The XRD pattern, SEM image and TEM image of the prepared MWCNT-SiO$_2$ nanohybrid pursuant to the teachings of the present embodiment example are illustrated in the aforedescribed FIG. 2, parts c and d, and FIG. 3, part b, of the DRAWINGS, respectively. The silica nanoparticles insertion into the MWCNTs structure can be observed from the XRD pattern shown in FIG. 2, part c. In addition, the nanoparticles' dispersion through the MWCNTs structure is abundantly clear from the depictions in FIG. 2, part d and FIG. 3, part b.

Example 4: Synthesis of the MWCNT-Alumina Nanohybrids Through Hydrothermal Method Aided by Ammonia Solution In this embodiment example, about 1.6 g AlCl$_3$ was first dissolved in about 100 ml of distilled water at room temperature (designated hereinafter as "solution A"). Separately, about 0.8 g sorbitol and about 0.3 g urea were dissolved in about 1.6 g ammonia solution (designated hereinafter as "solution B"). Therefore, solution B was added drop wise into the solution A and pH of the mixture was adjusted at 10. Then, about 0.23 g of open-capped MWCNTs was added to the reaction mixture and the mixture was added to the Teflon-lined hydrothermal cell for about 24 hours at about 140° C. Finally, the product was filtered and washed several times with distilled water and dried in the oven at about 60° C.

Figure 4:
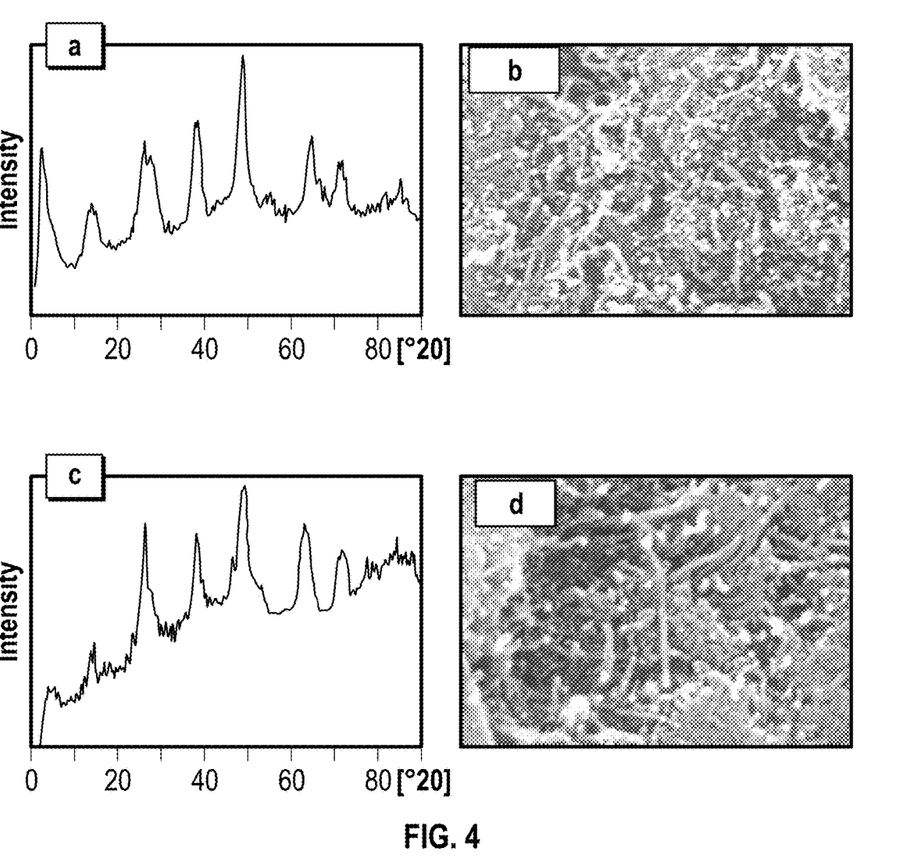
FIG. 4 also shows characterization analyses results, but for the prepared MWCNT-Alumina nanohybrid samples by a hydrothermal method by ammonia solution pursuant to the teachings of the present invention, as described in more detail in connection with EXAMPLE 3, which include: an XRD pattern, as shown in part a, and a scanning electron microscope (SEM) image, as shown in part b, respectively.
Figure 5:
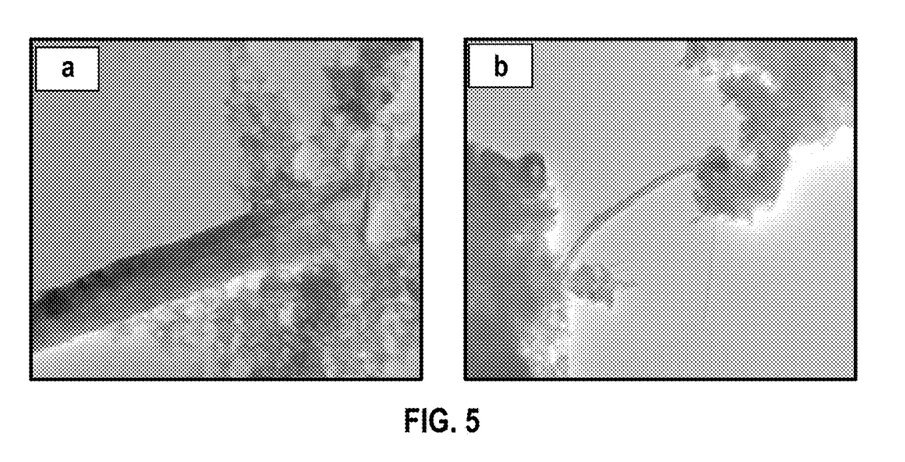
FIG. 5 shows transmission electron microscope (TEM) images of MWCNT-Alumina nanohybrid samples prepared by the methods described in more detail in connection with EXAMPLE 3, shown in part a, and EXAMPLE 4, shown in part b, respectively.

With reference now to FIG. 4 of the DRAWINGS, there are shown pairs of an XRD pattern and SEM image of the aforedescribed prepared MWCNT-Alumina nanohybrids, respectively, as depicted in respective parts a, b, c and d. With reference now to FIG. 5 of the DRAWINGS, there are shown TEM images of the aforementioned MWCNT-Alumina nanohybrid produced by the methods described herein, where part a corresponds to the nanohybrids constructed pursuant to EXAMPLE 3, and where part b corresponds to the nanohybrids constructed pursuant to EXAMPLE 4. As seen in both parts a and b of FIG. 5, the alumina nanoparticles are well dispersed and inserted into the structures of the MWCNTs. As can also be seen, alumina nanoparticles are attached within and on the surfaces of the MWCNTs. As discussed, the formation of this multi-faceted, multi-dimensional and multi-constitutional structure is superior to the inventions disclosed in the prior art, where nanoparticles coat only the surface of the MWCNTs.

Example 5: Synthesis of the MWCNT-Alumina Nanohybrids Through a Hydrothermal Method Aided by Sodium Hydroxide Here, about 7 g AlCl$_3$ was dissolved in about 50 ml of distilled water at room temperature (designated as solution A). Therefore, about 5 g NaOH was dissolved in about 30 ml of distilled water (designated as solution B). Then, solution B was dropped into the solution A. Afterwards, about 1.2 g sorbitol and about 0.4 g urea was dissolved in about 100 ml of distilled water, and added to the mentioned mixture. Continuously, about 0.9 g of the prepared open-capped MWCNTs was added, and the mixture was stirred. After about 24 hours mixing, the mixture was then added to a Teflon-lined hydrothermal cell for 48 h at about 140° C. The resultant product was filtered and washed several times with distilled water, dried in oven at about 60° C.

The XRD pattern, SEM image and TEM image of the aforedescribed prepared MWCNT-Alumina nanohybrid pursuant to the teachings in the instant example are respectively illustrated in the aforedescribed parts c and d of FIG. 4 and part b of FIG. 5 of the DRAWINGS. The XRD pattern (part c of FIG. 4) demonstrates the existence of both MWCNT and Alumina nanoparticles in the sample. With reference again to part d of FIG. 4 of the DRAWINGS, the MWCNT can be seen together with Alumina white spherical nanoparticles in a same structure, as depicted in the SEM analysis.

Example 6: Nanohybrid-Stabilized Emulsification

Figure 6:
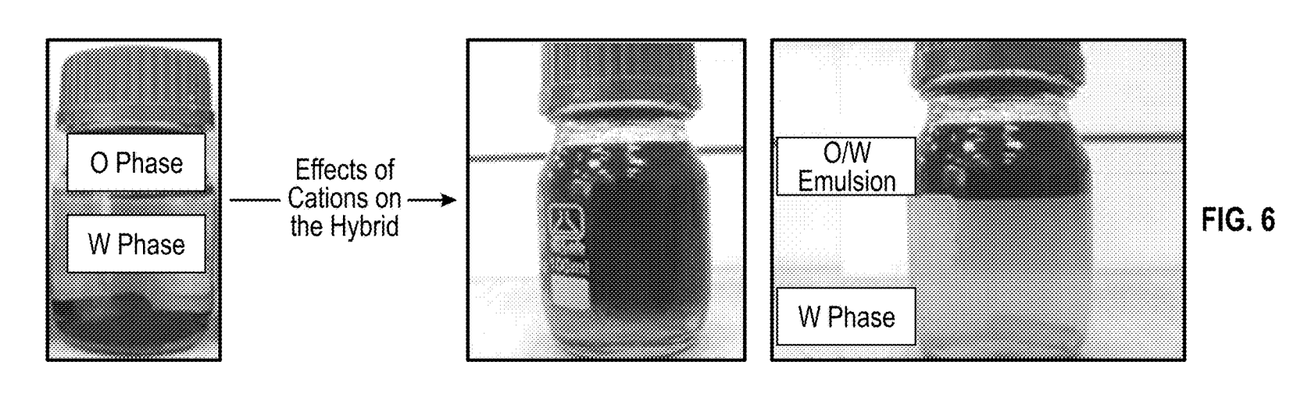
FIG. 6 illustrates sedimentation of a nanohybrid sample from the beginning of immersion (left vial) and spontaneous emulsification of oil-in-water (O/W) that tends to be placed in the interface by stirring (right vial)

In this exemplary embodiment of the present invention, the emulsification properties of the prepared nanohybrids are described. It was observed that the aforementioned nanohybrids exhibited very different behavior in de-ionized water and in salt-containing water media. For example, in the de-ionized water, the nanohybrid was totally hydrophilic and exhibited very high stability. This behavior of the nanohybrid can be explained by the hydrophilicity of the aforementioned functionalized MWCNT. Contrary to deionized water, the nanohybrid tended to form sediments in the salt-containing water to the extent that proper distribution of the particles was not possible even by ultrasonication. However, the nanohybrid behavior was changed after a while (about 12 days) and particles migrated to the interface to form a Pickering emulsion spontaneously. It should be noted that the emulsion formation time taken for the distribution of nanohybrid depends on distribution methods. With reference now to FIG. 6 of the DRAWINGS, there is illustrated a series of vials, demonstrating the spontaneous emulsification of O/W by the prepared MWCNT/Silica nanohybrids due to the effect of the dissolved ions in brine on nanohybrid behavior.

A. The Effect of Various Salts in Water on Nanohybrid Behavior

Herein, the change in nanohybrid behavior due to the interaction with water dissolved ions is studied at microscopic and macroscopic scales. At the macroscopic scale, a change from amphiphobicity to amphiphilicity can be observed, while at the microscopic scale, the changes occur in the structure, surface charges, and functional groups of the nanohybrid.

Macroscopic Study

In salt-containing water/oil systems, the type of cations in the water affects the formation of stable emulsion. The samples prepared in brines, according to the compositions shown in Tables 1 and 2 hereinbelow, display the effect of various cations and ions interaction on the formation of a Pickering emulsion in the presence of the prepared MWCNT/Silica nanohybrids in the present invention.

TABLE 1

Concentration of ions in water in various synthesized brine samples.

| Sample | $Ca^{2+}$ (mg/L) | $Mg^{2+}$ (mg/L) | $Na^+$ (mg/L) |
|---|---|---|---|
| a | 0 | 0 | 0 |
| b | 0 | 0 | 40000 |
| c | 3000 | 750 | 0 |
| d | 6000 | 1500 | 0 |
| e | 6000 | 1500 | 10000 |

TABLE 2

Concentration of cations in formation water taken from southwestern oil fields in Iran.

| Sample | $Ca^{2+}$ (mg/L) | $Mg^{2+}$ (mg/L) | $Na^+$ (mg/L) | $K^+$ (mg/L) | $Sr^{2+}$ (mg/L) | Oil (mg/L) |
|---|---|---|---|---|---|---|
| f | 9400 | 2420 | 29900 | 270 | 1715 | 113 |
| g | 11650 | 3061 | 31100 | 4 | 15 | 42 |

Figure 7:
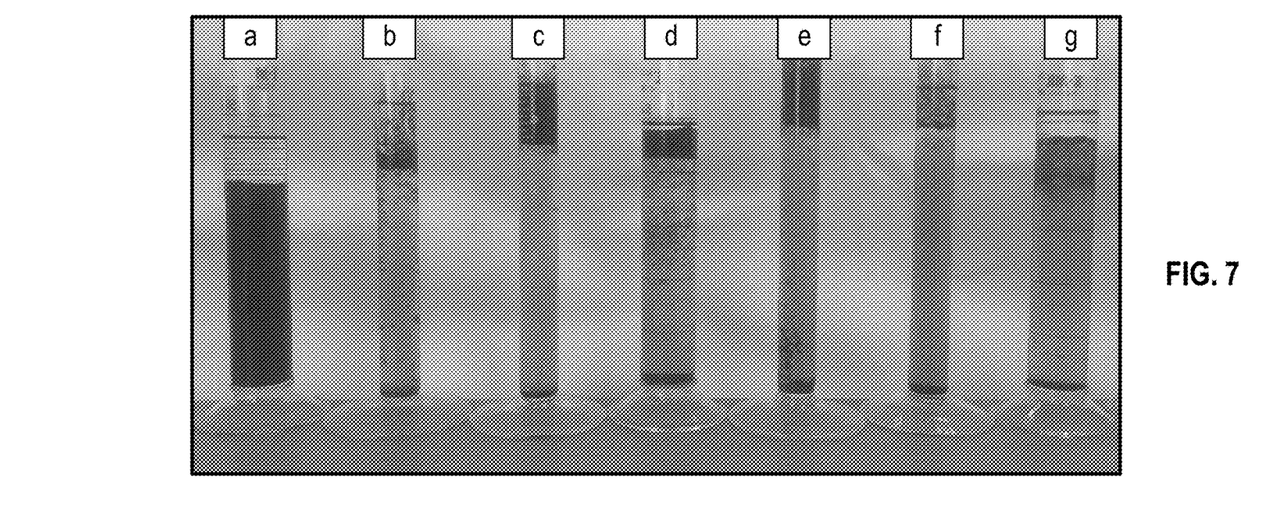
FIG. 7 depicts a two-phase system series in different brine samples with various ion compositions.
Figure 8:
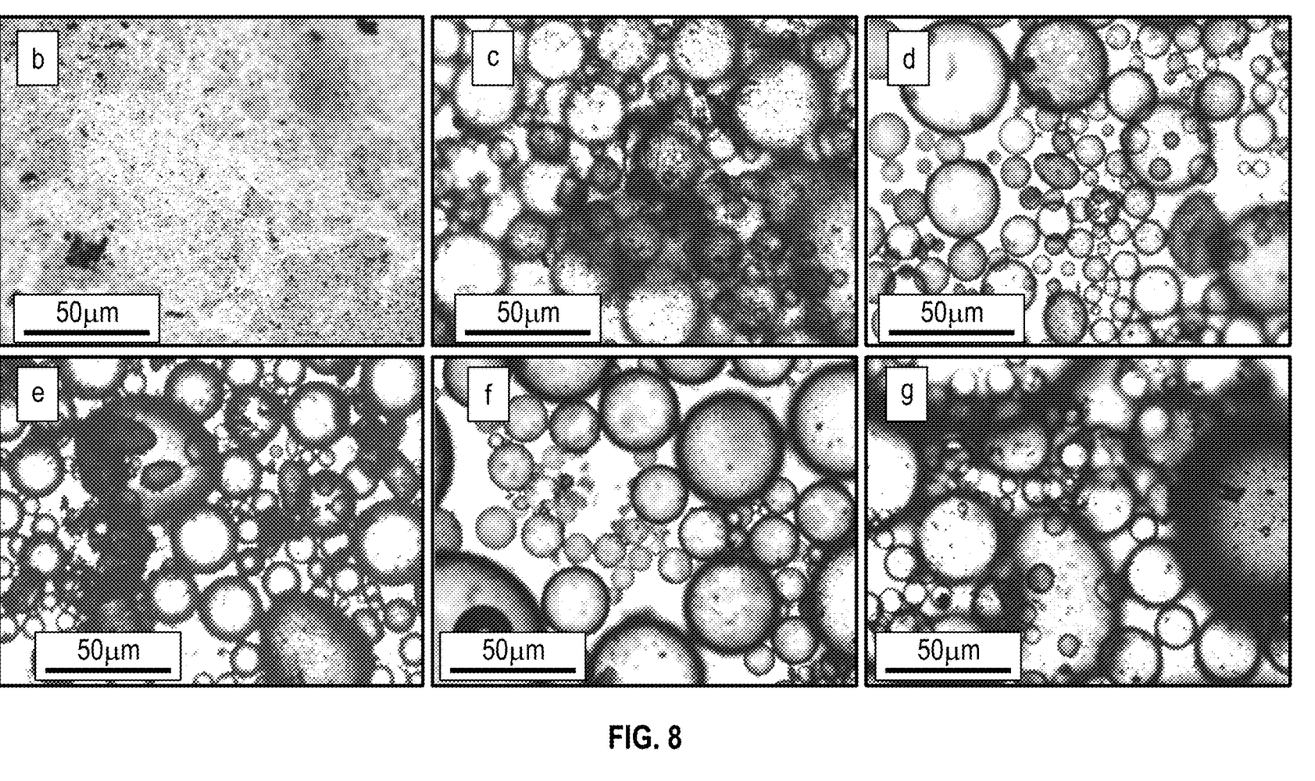
FIG. 8 illustrates various optical microscopic images from a water and oil interface and the emulsion stabilized by so-prepared MWCNT-silica nanohybrids in the present invention having a concentration of 0.1%.

With reference now to FIG. 7 of the DRAWINGS, there are depicted a series of brine samples (a) to (g), which demonstrate a two phase system of the aforementioned produced sample series. Accordingly, images of oil in water drops taken by the optic microscope are illustrated in FIG. 8 of the DRAWINGS for each of the aforesaid samples, particularly images (b)-(g). According to the data presented in Table 1, sample b consists of only a single ion. By comparing FIGS. 7 and 8, it is found that although an $Na^+$ ion changes the charges on the nanohybrid and forces the particles to migrate to the interface, it does not lead to the creation of a water and oil emulsion. Sample b is a representative for a series of experiments in which the effect of various concentrations of an $Na^+$ ion has been studied on the nanohybrid behavior. No emulsion formation was observed in an $Na^+$ single ion system in the concentration range of about 500 mg/L to 40000 mg/L.

With further reference now to FIGS. 7 and 8 of the DRAWINGS, the exemplary tests results show that magnesium and calcium ions are individually able to change the nanohybrid and force ions to migrate to the interface of the two phases and to create a stable emulsion. Because magnesium and sodium ions are approximately similar in size, it seems that the type of ionic charge is the most important parameter in changing the structural behavior. Studies also reveal that the ions bring about irreversible changes in the nanohybrid.

The effect of ion interactions on the nanohybrid behavior was also studied in multi-ionic systems, i.e., sample e in FIGS. 7 and 8. It appears that the sodium ions did not disturb the magnesium and calcium ions. The images, taken by an optic microscope, show that the drop size in all systems is approximately equal. In addition, the nanohybrid emulsification behavior was studied in formation water (f and g samples), where a stable emulsion was formed as an intervening phase.

Microscopic Study

Accordingly, the change in the stability of the material in water from a very stable to an unstable condition was studied by analyzing the changes in zeta potential of the structure. In order to study zeta potential, two samples were prepared through ultrasonic and stirring methods. One of the samples was put in de-ionized water (sample a) while the other was immersed in salt-containing water with sample "e" concentration, as shown in Table 1 (sample b).

Thus, sample b was immersed in salt-containing water, then removed after about 3 hours and rinsed with deionized water for a few times. Then, the sample was distributed by ultrasonication and then it was subjected to the aforementioned zeta test.

Figure 9:
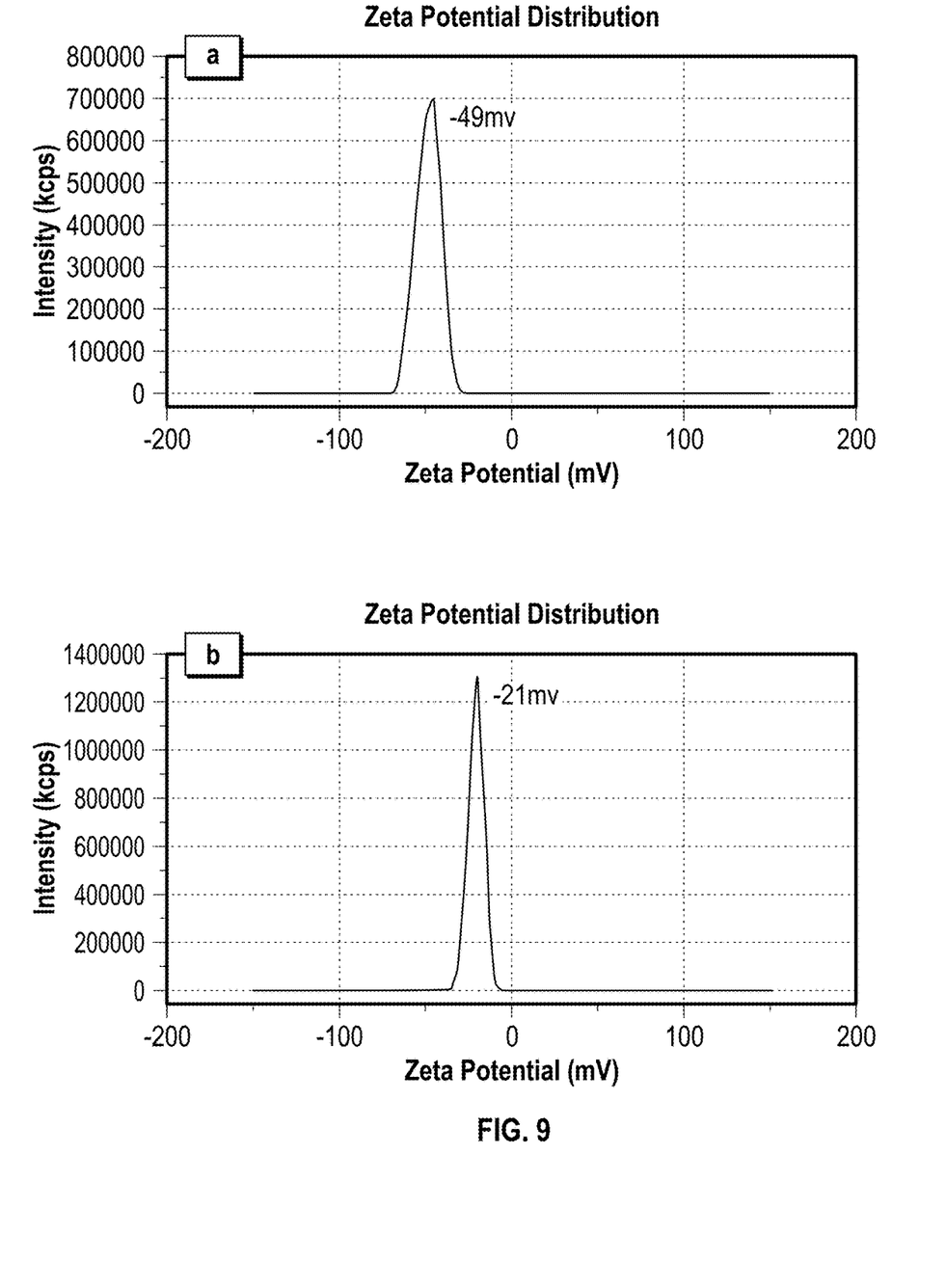
FIG. 9 illustrates zeta potential values for equal concentrations of the aforementioned preparation of MWCNT-silica nanohybrids: a nanohybrid in an ion-free environment, as illustrated in part a, and a nanohybrid after the effect of ions, as depicted in part b.

With reference now to FIG. 9 of the DRAWINGS, parts a and b thereof depict the zeta potential variations. According to part a, the zeta potential of the structure, once not being under the influence of the cations, corresponds to −49 mV, which indicates a perfect stabilization and reflects the hydrophilicity of the structure, whereas part b pertains to the case where the structure is affected by cationic interactions causing a zeta potential equal to −21 mV, which implies a reduction in hydrophilicity for the nanohybrid structure. With further reference to FIG. 9, there are shown great changes in zeta potential in both samples, which implies that the structure charge is affected by dissolved cations to the extent that it is transformed from a stable structure to a very unstable one. This demonstrates the effect of dissolved ions on the charges of the particles in water.

Figure 10:
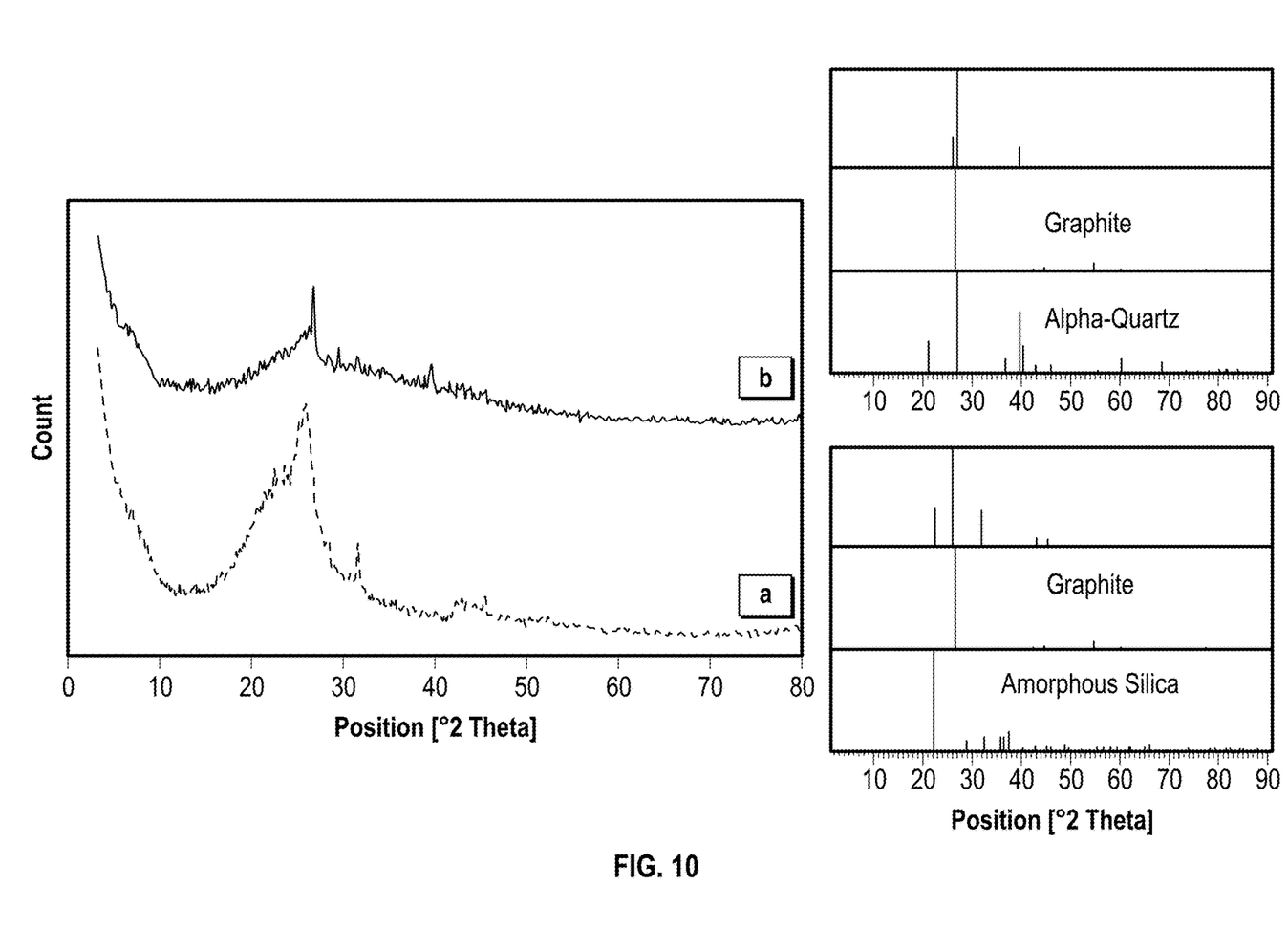
FIG. 10 illustrates an XRD analysis and a peak list of the structure before and after the effect of ions: where part a thereof illustrates a nanohybrid before the effect of ions on its structure, where the silica structure is seen in amorphous form, and part b which illustrates a nanohybrid after the effect of ions on its structure, where the nanohybrid has an alpha quartz structure.

The structure was also studied by using XRD analysis both before and after being immersed in salt-containing water. Both samples were dried at about 60° C. for about 48 hours in order to prevent the deformation of silica structure due to the high temperature. An analysis result shown in FIG. 10 of the DRAWINGS illustrates that when the sample was immersed in salt-free water, an orthorhombic structure, as the metastable form of silica, was formed. However, when the sample was immersed in water, the analysis showed an alpha quartz structure. This change was likely due to the effect of water ions on the structure, and by the overlap of various plates formed during the production of nanohybrid, which was detected in the XRD analysis.

Therefore, it is concluded that nanohybrids are activated in the presence of high concentration of cations existing in water, usually found in formation waters, and they are able to create a Pickering emulsion. Bivalent cations, such as magnesium and calcium, change the hydrophilic-lipophilic balance more intensely than the univalent cation such as sodium. The emulsion formed by the nanohybrids of the instant invention is very stable and is formed automatically, without the need for emulsifiers or mechanical mixing.

B. The Effect of Mixing Conditions on Emulsification Time

It should be understood that the mode of mixing of the nanohybrids with water affects the rate of emulsification significantly. In this analysis, three types of mixing techniques between nanohybrids and water were studied: (1) without using a mechanical stirrer or ultrasonic homogenizer, (2) using a mechanical stirrer, and (3) using an ultrasonic homogenizer and a mechanical stirrer. The aforementioned triple-categorized study is important because it shows that the nanohybrid has the potential to change its behavior even in the absence of mixing, although it requires more time. This can be effective in the application of these materials in EOR processes, where mechanical mixing is not available. The mixing method is effective in two ways, including the rate of nanohybrid distribution in water and interactions between the nanohybrid structure and ions dissolved in water.

Accordingly, in the first experiment, the nanohybrid was put into salt-containing water without employing any type of stirrer. The nanohybrid remained as a sediment in water for a very long time, but after about 12 days, the nanohybrid behavior changed from amphiphobic to amphiphilic. The behavior change occurred much faster when a stirrer was used. The change in nanohybrid behavior could be observed after about 12 hours when a mechanical stirrer (about 400 rpm) was used. The ultrasonic bath had a greater effect than the mechanical stirrer. The results were repeated by using a homogenizer for about 15 minutes (with a power of about 300 W at room temperature) and then using a mechanical stirrer for about 3.5 hours. The difference in the termination rate of the nanohybrid agglomeration condition in these three methods may be an explanation for the contact taking place between the nanohybrid surface and ions dissolved in water, and speeds up their interaction. This study is important because it shows that the nanohybrid has the potential to change its behavior even in the absence of mixing although it requires more time. As discussed, this property can be quite effective in the application of these materials in EOR processes, where mechanical mixing is impractical or not available. The mixing method is effective through two ways, including: the rate of nanohybrid distribution in water, and interactions between the nanohybrid structure and ions dissolved in water.

Example 7: Nanofluid Preparation

For the preparation of a nanofluid with the aforedescribed prepared MWCNT-SiO$_2$ nanohybrid in order to evaluate the contact angle and interfacial tension properties, about 0.2 g of the nanohybrid sample was dispersed in water ultrasonically. These nanofluids are stable without using any surfactant or co-surfactant for several months.

Example 8: Determination of the Interfacial Tension (IFT)

In this exemplary embodiment of the present invention, the effect of the nanohybrids prepared pursuant to the methods described in the present invention on the aforementioned oil/water interfacial tension (IFT) was investigated. It should be understood that for the experiments related to core oil, oil rock should be saturated with model oil (kerosene) and nanoparticles. The aforedescribed prepared nanohybrid (about 0.2 wt %) was dispersed in water without surfactant for the evaluation of the nanofluid surface tension. This nanofluid was found to have good stability at about 70° C. (which generally corresponds to reservoir conditions). A mixture of water and kerosene was prepared as the reference sample. The surface tension between water and kerosene (reference sample) was obtained as about 53.9 mN/m.

Figure 11:
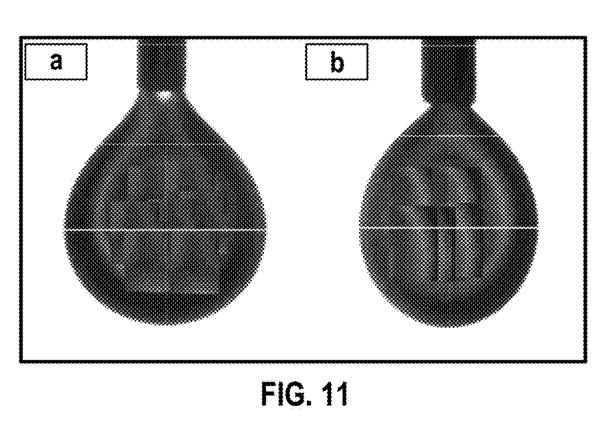
FIG. 11 shows: a water drop in kerosene, as shown in part a, and a nanofluid drop in kerosene, as depicted in part b.

With reference now to FIG. 11 of the DRAWINGS, there are shown parts a and b thereof, illustrating water and nanofluid droplet photos in kerosene, respectively. The resultant values of interfacial tension of the nanofluids containing the aforedescribed MWCNT-SiO$_2$ and MWCNT-Al$_2$O$_3$ nanohybrids, particularly as synthesized according to the aforementioned EXAMPLEs 2-5, are set forth and presented in Table 3 hereinbelow. It can be observed that the surface tension between nanofluids containing the MWCNT-SiO$_2$ nanohybrids, as prepared by the method described in EXAMPLE 2, and kerosene was found to be about 27.5 mN/m. Therefore, the aforementioned MWCNT-SiO$_2$ nanohybrids, as prepared by the ultrasound-assisted sol-gel method, can decrease the reference sample surface tension in about half without any surfactant or emulsion stabilizer. As can also be seen in Table 3, the nanofluid, that is the nanohybrid prepared by the aforedescribed hydrothermal method in the presence of NaOH, can obviously decrease the interfacial tension without any surfactant or co-surfactant.

TABLE 3

The effect of nanohybrids on the Interfacial tension (IFT) values between aqueous and oil phases

| Interfacial tension | (mN/m) |
|---|---|
| Interfacial tension between distilled water and Kerosene | 53.9 |
| Interfacial tension between EXAMPLE 2 and Kerosene | 27.5 |
| Interfacial tension between EXAMPLE 3 and Kerosene | 53.6 |
| Interfacial tension between EXAMPLE 4 and Kerosene | 51.7 |
| Interfacial tension between EXAMPLE 5 and Kerosene | 37.8 |

Example 9: Determination of the Contact Angle

In this exemplary embodiment of the present invention, the effect of the nanohybrids prepared pursuant to the methods described in the present invention on the reservoir rocks wettability was investigated. For this purpose, two types of rocks (carbonate and sand stone) were selected for contact angle evaluation tests.

Before the tests, the sample rocks were soaked in kerosene and dried in an oven at about 40° C. Then, the rocks were taken in a water media so that the kerosene droplet was injected on the rock surface by a syringe and the contact angle was determined with proper optical equipment to measure the angles, as is understood in the art.

Figure 12:
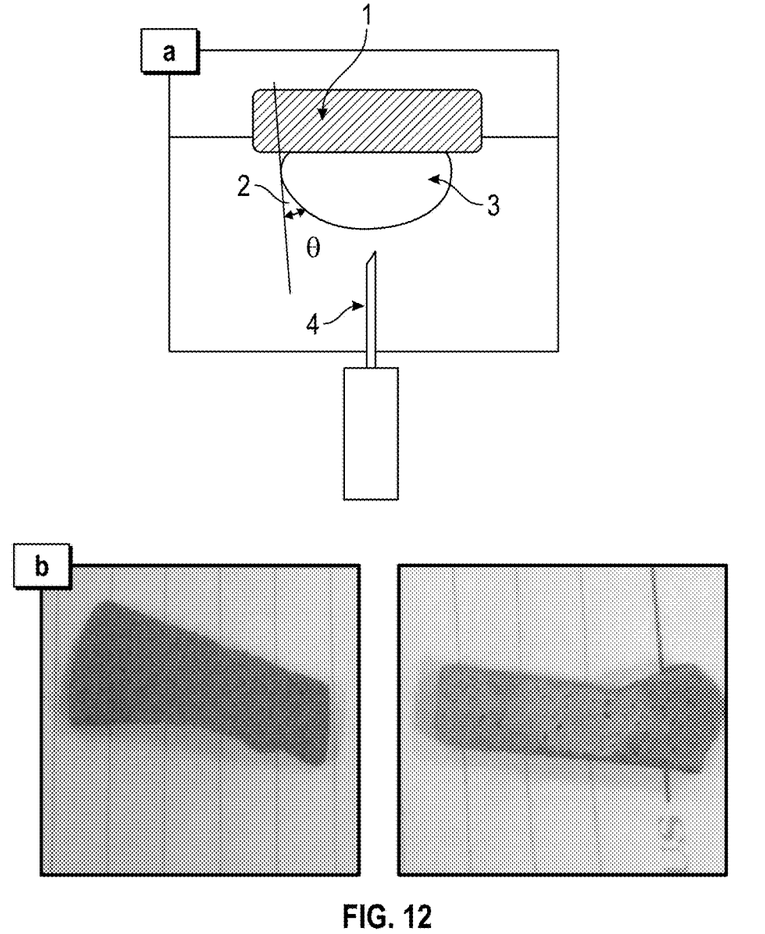
FIG. 12 shows schematic representations of: contact angle measurements in oil media, which include: 1) a reservoir rock saturated of kerosene and nanofluid, 2) distilled water, 3) a kerosene drop, and 4) an injection syringe of kerosene, as shown in part a; and reservoir rock samples 3 days after immersion in a nanofluid: 1) a sand stone saturated with a nanohybrid, and 2) a carbonate rock saturated with a nanohybrid, as depicted in part b thereof.

With reference now to FIG. 12 of the DRAWINGS, there are shown samples. It should be considered that in this condition, the contact angle values that are over and that are below 90° C. represent the more hydrophilic and the more hydrophobic samples, respectively, as shown in part a. For evaluating the effect of the aforedescribed nanohybrids, in addition to kerosene, the rocks were saturated in a nanofluid separately. After three days, a layer of nanohybrid could be seen on the rock surface, as depicted in part b.

Figure 13:
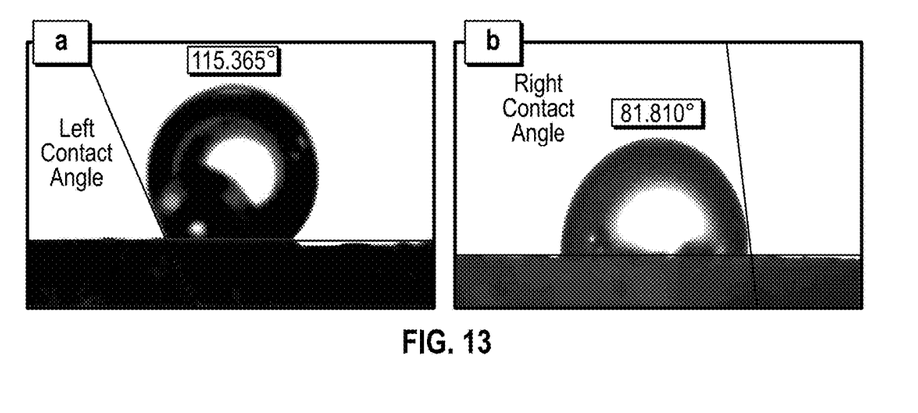
FIG. 13 illustrates measurement of contact angles for two situations: between a kerosene drop and sand stone, as shown in part a, and between a kerosene drop and carbonate rock, as depicted in part b thereof.

With reference now to FIG. 13 of the DRAWINGS, there are shown respective contact angle measurements between kerosene and the rocks which are saturated only in kerosene. As can be seen in part a thereof, the contact angle between kerosene and sandstone rock was determined to be about 115°. In addition, the same measurement for carbonate rock was determined to be about 82° as shown in part b.

In a second series of experiments, the rocks were initially saturated in kerosene and in a nanofluid (consisting of about 0.2 wt % of nanohybrids), respectively, and then the contact angle between the kerosene and the rocks were determined. Using nanofluids containing MWCNTs/Silica nanohybrids, as prepared by the methods according to the EXAMPLES 2 and 3 hereinabove, the contact angle between kerosene and rock samples were determined as shown in FIG. 14 of the DRAWINGS, particularly parts a-d thereof.

Figure 14:
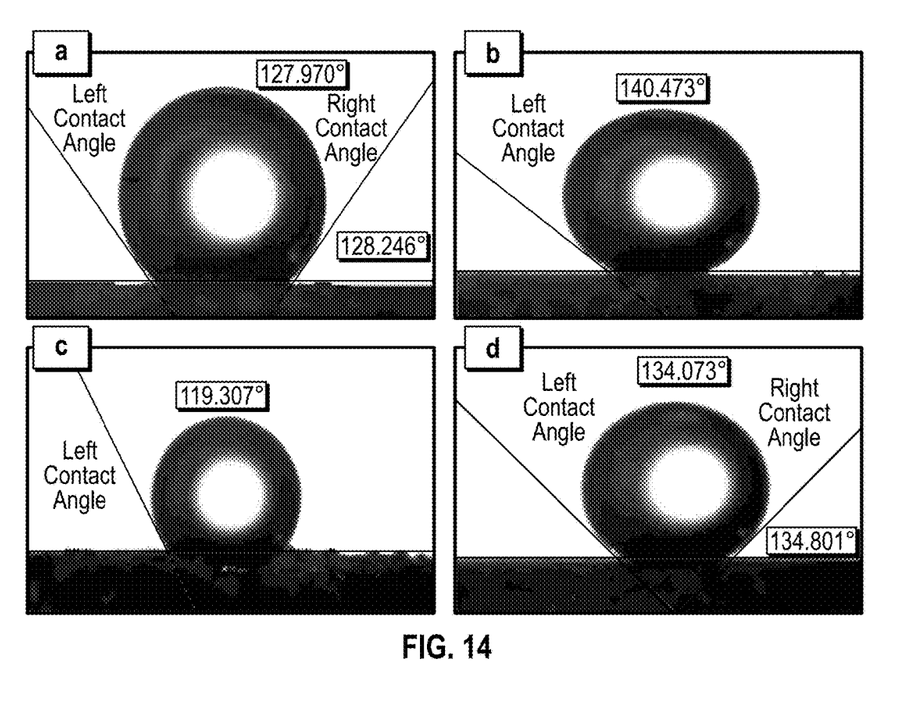
FIG. 14 illustrates measurements of contact angles between kerosene drops and reservoir rock samples with a layer of nanofluids containing the aforementioned MWCNTs/Silica nanohybrids prepared pursuant to the methods described in the present invention, for situations of: (a) sand stone rock using a nanohybrid, as described in more detail in connection with Example 2, as shown in part a thereof, (b) carbonate rock using a nanohybrid, as also described in more detail in connection with Example 2, as illustrated in part b, (c) sand stone rock using a nanohybrid, as described in more detail in connection with Example 3, as depicted in part c, and (d) carbonate rock using a nanohybrid, as also described in more detail in connection with Example 3, as shown in part d.

Using the MWCNTs/Silica nanohybrids produced according to the method described in EXAMPLE 2, the contact angle was found to be about 128° and 140° for the aforesaid sandstone and carbonate rock samples, respectively, as depicted in parts a and b of FIG. 14 of the DRAWINGS. While, the same contact angle measurements using MWCNTs/Silica nanohybrids produced according to method described in EXAMPLE 3 was found to be about 119° and 134° for sandstone and carbonate rock samples, respectively, as depicted in parts c and d thereof.

Figure 15:
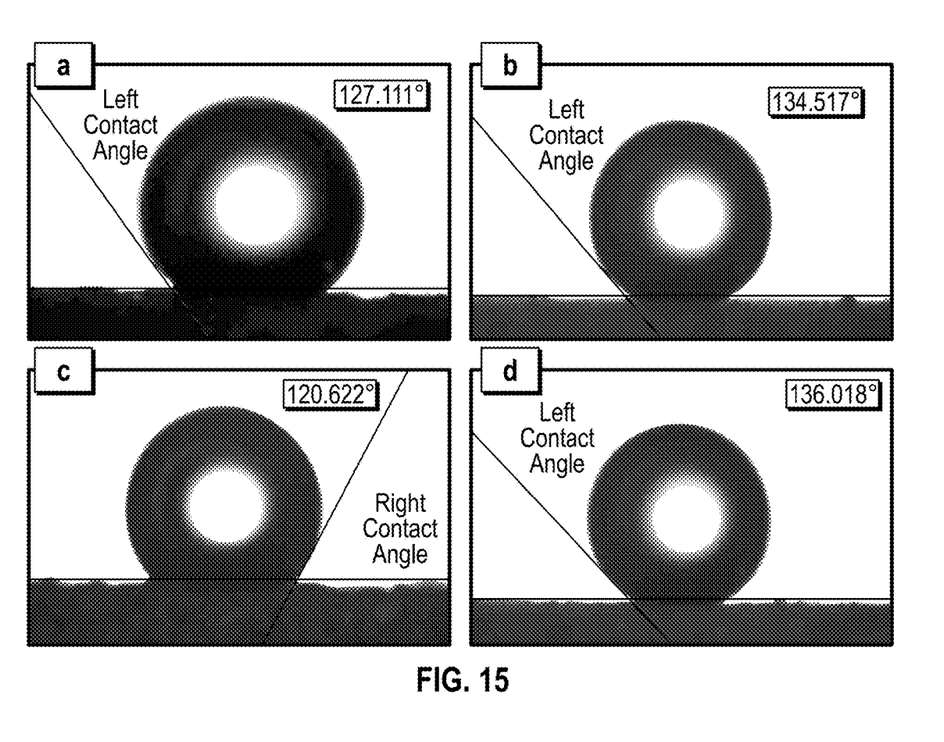
FIG. 15 shows measurements of contact angles between kerosene drops and reservoir rock samples with a layer of nanofluids containing the aforementioned MWCNTs/Alumina nanohybrids prepared pursuant to the methods described in the present invention, for situations of: (a) sand stone rock using a nanohybrid, as described in more detail in connection with Example 4, as shown in part a thereof, (b) carbonate rock using a nanohybrid, as also described in more detail in connection with Example 4, as illustrated in part b, (c) sand stone rock using a nanohybrid, as described in more detail in connection with Example 5, as depicted in part c, and (d) carbonate rock using a nanohybrid, as also described in more detail in connection with Example 5, as shown in part d.

Similar wettability test results determined by contact angle evaluation in the presence of MWCNTs/Alumina nanohybrids, as prepared by the methods according to the EXAMPLEs 4 and 5 hereinabove are shown in FIG. 15 of the DRAWINGS, particularly parts a-d thereof. As can be observed in this figure, the contact angle is about 127° and 135° for the aforesaid sandstone and carbonate rock samples, respectively, by using nanohybrids of EXAMPLE 4, as depicted in parts a and b. Furthermore, the contact angle measurements using nanohybrids produced according to method described in EXAMPLE 5 was found to be about 121° and 136° for the aforesaid sandstone and carbonate rock samples, respectively, as depicted in parts c and d.

The abovementioned contact angle data are summarized and set forth in Table 4 herein below, where the respective contact angle measurements are increased, pursuant to the various embodiments of the present invention.

TABLE 4

The effect of the prepared MWCNTs/Silica (or Alumina) nanohybrids on reservoir rocks wettability

| Nanohybrid | Rock type | contact angle | In comparison With the reference test |
|---|---|---|---|
| — (reference test) | Sandstone | 115 | — |
|  | Carbonate | 82 | — |
| MWCNTs/Silica prepared according to EXAMPLE 2 | Sandstone | 128 | 13° |
|  | Carbonate | 140 | 58° |
| MWCNTs/Silica prepared according to EXAMPLE 3 | Sandstone | 119 | 4° |
|  | Carbonate | 134 | 52° |
| MWCNTs/Alumina prepared according to EXAMPLE 4 | Sandstone | 127 | 12° |
|  | Carbonate | 134 | 52° |
| MWCNTs/Alumina prepared according to EXAMPLE 5 | Sandstone | 121 | 6° |
|  | Carbonate | 136 | 54° |

While the present invention has been illustrated by the description of the embodiments thereof, and while the embodiments have been described in detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the breadth or scope of the applicant's concept. Furthermore, although the present invention has been described in connection with a number of exemplary embodiments and implementations, the present invention is not so limited but rather covers various modifications and equivalent arrangements, which fall within the purview of the appended claims.

What is claimed is:

1. A method for the preparation of a binary hydrophilic-hydrophobic nanohybrid comprising:
   modifying a plurality of multi-walled carbon nanotubes (MWCNTs) such that at least one end of each MWCNT is in an open configuration;
   synthesizing a plurality of inorganic nanoparticles and, as synthesis occurs, substantially simultaneously encapsulating at least a first portion of the plurality of inorganic nanoparticles within the plurality of MWCNTs; and
   forming an admixture of the binary hydrophilic-hydrophobic nanohybrids that include the first portion of inorganic nanoparticles encapsulated within the MWCNTs, the MWCNTs comprising an outermost structure of the nanohybrids.

2. The method according to claim 1, wherein modifying the plurality of MWCNTs includes enhancing a hydrophilicity of each MWCNT.

3. The method according to claim 1, wherein the MWCNTs have a length of about 10 micrometers and a diameter of about 10 nm to about 20 nm.

4. The method according to claim 1, wherein the modifying of the plurality of MWCNTs includes employing a reflux reaction with only one type of inorganic acid.

5. The method according to claim 4, wherein the inorganic acid is nitric acid.

6. The method according to claim 1, wherein the inorganic nanoparticles are selected from the group consisting of silica nanoparticles, alumina nanoparticles and combinations thereof.

7. The method according to claim 1, wherein the inorganic nanoparticles have a size less than 100 nm.

8. The method according to claim 7, wherein the inorganic nanoparticles have a size less than 50 nm.

9. The method according to claim 1, wherein the MWCNTs to the inorganic nanoparticles weight ratio in the admixture is less than or about 0.3.

10. The method according to claim 1, wherein, in the synthesizing the plurality of inorganic nanoparticles, the plurality of inorganic nanoparticles are synthesized via process that is selected from the group consisting of a sol-gel method, a sol-gel method assisted by ultrasonication and a hydrothermal method.

11. The method according to claim 1, wherein, in the synthesizing the plurality of inorganic nanoparticles, the plurality of inorganic nanoparticles are synthesized via a hydrothermal method assisted by a chemical compound that is selected from the group consisting of ammonia, sodium hydroxide, and combinations thereof.

12. A binary hydrophilic-hydrophobic nanohybrid produced by the method according to claim 1.

13. The method according to claim 1, wherein the plurality of inorganic nanoparticles includes silicon dioxide.

14. The method according to claim 1, further comprising attaching a second portion of the plurality of inorganic nanoparticles on a surface of the MWCNTs.

15. The method according to claim 1, wherein the nanohybrids are configured to increase a contact angle by approximately 50-60 degrees in carbonated rocks.

* * * * *